United States Patent [19]

Spencer et al.

[11] Patent Number: 5,328,823
[45] Date of Patent: Jul. 12, 1994

[54] ENZYME-BASED BIOSENSORS FOR DETECTING NOBLE GASES

[75] Inventors: Kevin C. Spencer, Hinsdale; Christine E. Boisrobert, Chicago, both of Ill.

[73] Assignee: American Air Liquide, Walnut Creek, Calif.

[21] Appl. No.: 982,500

[22] Filed: Nov. 27, 1992

[51] Int. Cl.⁵ .................... C12Q 1/00; G01N 21/00
[52] U.S. Cl. ........................ 435/4; 435/288; 435/291; 435/817; 422/83; 422/85; 422/89
[58] Field of Search ............ 435/4, 288, 291, 817; 422/83, 85, 89

[56] References Cited

U.S. PATENT DOCUMENTS

| | | | |
|---|---|---|---|
| 2,569,217 | 9/1951 | Bagdigian | 422/83 |
| 3,143,471 | 8/1964 | Coady | 167/78 |
| 3,183,171 | 5/1965 | Schreiner | 422/83 |
| 3,378,443 | 4/1968 | Cooper et al. | 167/78 |
| 3,677,024 | 7/1972 | Segall | 62/64 |
| 3,725,076 | 4/1973 | Stefanucci et al. | 422/83 |
| 3,957,892 | 5/1976 | Kleiman | 260/652.5 R |
| 4,008,754 | 2/1977 | Kraushaar et al. | 165/2 |
| 4,017,363 | 4/1977 | McMullen et al. | 435/94 |
| 4,044,004 | 8/1977 | Saucy et al. | 260/239.55 C |
| 4,136,049 | 1/1979 | Horiishi et al. | 252/62.56 |
| 4,138,565 | 2/1979 | Ehrhardt et al. | 544/346 |
| 4,308,264 | 12/1981 | Conway et al. | 424/236 |
| 4,314,810 | 2/1982 | Fourcadier et al. | 8/410 |
| 4,315,266 | 2/1982 | Ellis, Jr. | 343/895 |
| 4,450,960 | 5/1984 | Johnson | 206/334 |
| 4,496,397 | 1/1985 | Waite | 106/161 |
| 4,501,814 | 2/1985 | Schoenrock et al. | 435/94 |
| 4,548,605 | 10/1985 | Iwamoto et al. | 604/410 |
| 4,622,425 | 11/1986 | Gagne | 562/595 |
| 4,664,256 | 5/1987 | Halskov | 206/213.1 |
| 4,721,677 | 1/1988 | Clark, Jr. | 435/291 |
| 4,812,320 | 3/1989 | Ruzek | 426/393 |
| 4,830,858 | 3/1989 | Payne et al. | 424/450 |
| 4,892,579 | 1/1990 | Hazelton | 75/0.5 B |
| 4,895,726 | 1/1990 | Curtet et al. | 424/456 |
| 4,895,729 | 1/1990 | Powrie et al. | 426/316 |
| 4,919,955 | 4/1990 | Mitchell | 426/394 |
| 4,946,326 | 8/1990 | Schvester et al. | 426/316 |
| 4,965,165 | 10/1990 | Saccocio et al. | 430/138 |
| 4,971,813 | 11/1990 | Strobel et al. | 426/51 |
| 5,004,623 | 4/1991 | Giddey et al. | 426/564 |
| 5,006,222 | 4/1991 | Sequeria, Jr. | 208/33 |
| 5,021,251 | 6/1991 | McKenna et al. | 426/330.5 |
| 5,030,778 | 7/1991 | Ransford | 570/208 |
| 5,045,529 | 9/1991 | Chiang | 514/6 |
| 5,064,070 | 11/1991 | Higashiyama | 206/455 |
| 5,108,656 | 4/1992 | Schvester et al. | 252/380 |
| 5,128,160 | 7/1992 | Fath et al. | 426/316 |

FOREIGN PATENT DOCUMENTS

| | | | |
|---|---|---|---|
| 989311 | 5/1976 | Canada | 167/322 |
| 0111595 | 6/1984 | European Pat. Off. | C13K 11/00 |
| 204532 | 12/1986 | European Pat. Off. | 436/15 |
| 0346201 | 12/1989 | European Pat. Off. | |
| 0412155 | 2/1991 | European Pat. Off. | |
| 0440273 | 8/1991 | European Pat. Off. | C12N 9/92 |
| 3007712 | 10/1981 | Fed. Rep. of Germany | |
| 1339669 | 9/1963 | France | |
| 1454653 | 8/1966 | France | |
| 2261518 | 9/1975 | France | |
| 2406567 | 5/1979 | France | |
| 2643232 | 8/1990 | France | |
| 52-27699 | 9/1972 | Japan | |
| 52-86987 | 7/1977 | Japan | |
| 52-97913 | 8/1977 | Japan | |
| 54-129185 | 10/1979 | Japan | |

(List continued on next page.)

OTHER PUBLICATIONS

Dragomir et al, *Biochimica et Biophysica Acta*, vol. 389, pp. 530–540, 1975.

(List continued on next page.)

Primary Examiner—Michael G. Wityshyn
Assistant Examiner—Abdel A. Mohamed
Attorney, Agent, or Firm—Oblon, Spivak, McClelland, Maier & Neustadt

[57] ABSTRACT

A method of detecting at least one noble gas through a semi-permeable membrane, allowing the permeating noble gas to contact an enzyme, the activity of which is changed by the noble gas, and detecting the change in enzyme activity.

22 Claims, 4 Drawing Sheets

FOREIGN PATENT DOCUMENTS

| | | |
|---|---|---|
| 1-059647 | 1/1980 | Japan . |
| 58-39650 | 3/1983 | Japan . |
| 60-56984 | 4/1985 | Japan . |
| 63-77848 | 4/1988 | Japan . |
| 2-104502 | 4/1990 | Japan . |
| 3-200568 | 9/1991 | Japan . |
| 1289437 | 2/1987 | U.S.S.R. . |
| 0415656 | 8/1934 | United Kingdom . |
| 1376362 | 12/1974 | United Kingdom . |
| 2029846 | 3/1980 | United Kingdom ............ C13L 1/10 |
| 2091556 | 8/1982 | United Kingdom . |

OTHER PUBLICATIONS

Barazana et al, *Analytical Biochemistry*, vol. 182, pp. 109-115, 1989.

Doebbler et al, *Federation Proceedings*, vol. 26, p. 650, Abstract No. 2209, 1967.

Sandhoff et al, *FEBS Letters*, vol. 62, No. 3, pp. 284-287, 1976.

Chemical Abstracts, vol. 68, No. 14, AN-60751j.
Chemical Abstracts, vol. 74, No. 23, AN-121276I.
Chemical Abstracts, vol. 76, No. 13, AN-70898s.
Chemical Abstracts, vol. 80, No. 7, AN-35579z.
Chemical Abstracts, vol. 80, No. 11, AN-56112g.
Chemical Abstracts, vol. 86, No. 3, AN-14672h.
Chemical Abstracts, vol. 87, No. 22, AN-172800y.
Chemical Abstracts, vol. 91, No. 17, AN-138183x.
Chemical Abstracts, vol. 93, No. 24, AN-225670p.
Chemical Abstracts, vol. 97, No. 18, AN-145890c.
Chemical Abstracts, vol. 98, No. 10, AN-78191f.
Chemical Abstracts, vol. 99, No. 21, AN-172397v.
Chemical Abstracts, vol. 106, No. 25, AN-210601e.
Chemical Abstracts, vol. 115, No. 20, AN-214644e.
WPI Abstracts, AN-70-84762R, DE-1753586.
WPI Abstracts, AN-82-05785E, DE-3 202 622, Sep. 9, 1982.

Federation Proceedings, vol. 27, No. 3, May-Jun. 1968, H. R. Schreiner, "General Biological Effects of The Helium-Xenon Series of Elements".

156 Food Technology, vol. 34, No. 6, Jun. 1980, p. 102.

Federation Proceedings, vol. 26, No. 2, Mar.-Apr. 1967, pp. 650, G. F. Doebbler, et al., "Inert Gas Interactions and Effects on Enzymatically Active Proteins".

Aviation, Space and Environmental Medicine, vol. 48, No. 1, Jan. 1977, pp. 40-43, S. K. Hemrick, et al., "Effect of Increased Pressures of Oxygen, Nitrogen, and Helium on Activity of a Na-K-Mg ATPase of Beef Brain".

Undersea Biomedical Research, vol. 17, No. 4, 1990, pp. 297-303, J. S. Colton, et al., "Effect of Helium and Heliox on Glutamate Decarboxylase Activity".

Sciences Des Aliments, vol. 4, No. 4, 1984, pp. 595-608, B. Picard, et al., "Effect of Nitrogen, Carbon Monoxyde and Carbon Dioxide on the Activity of Proteases of Pseudomonas Fragi and Streptomyces Caespitosus".

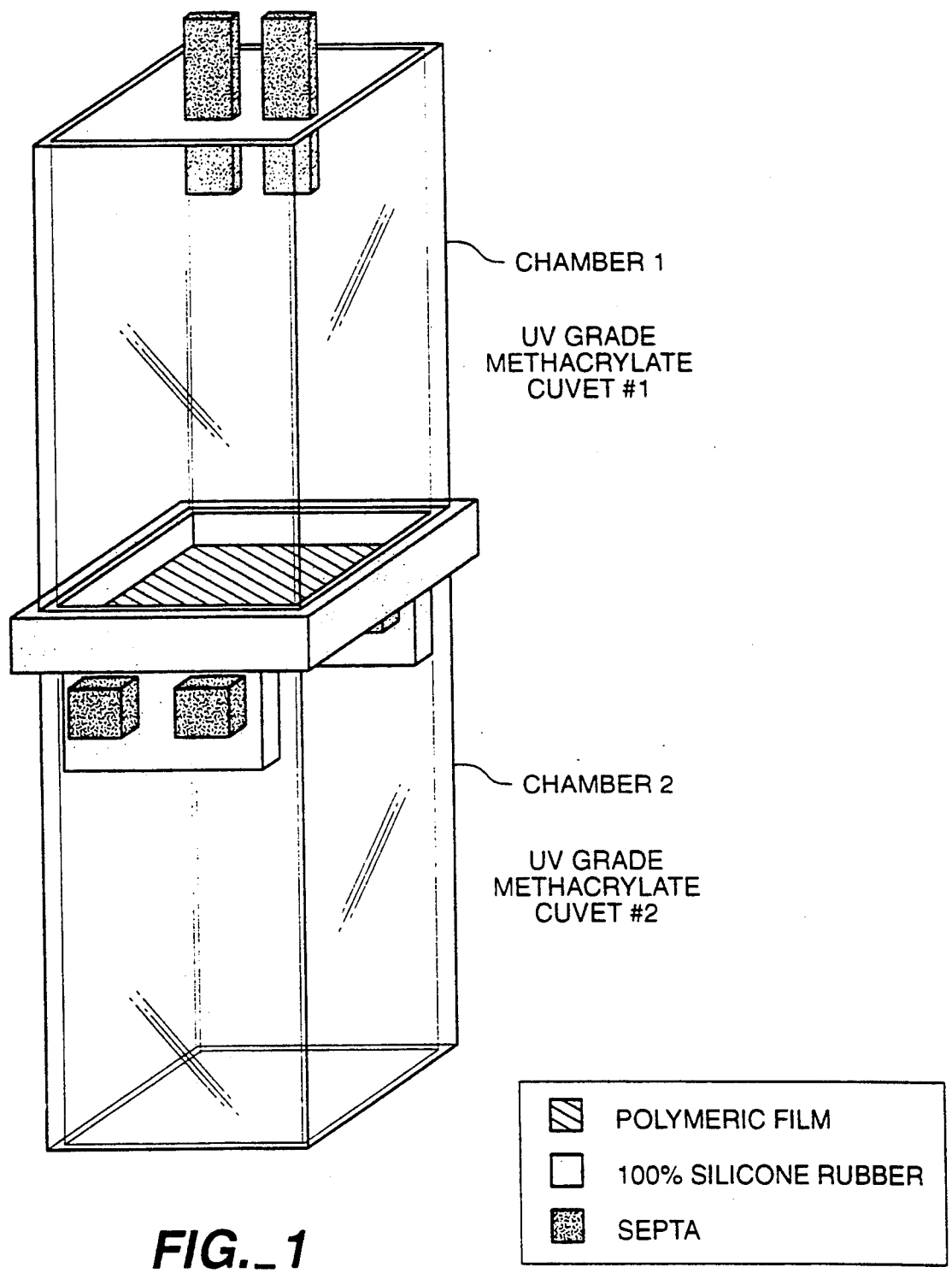
FIG._1

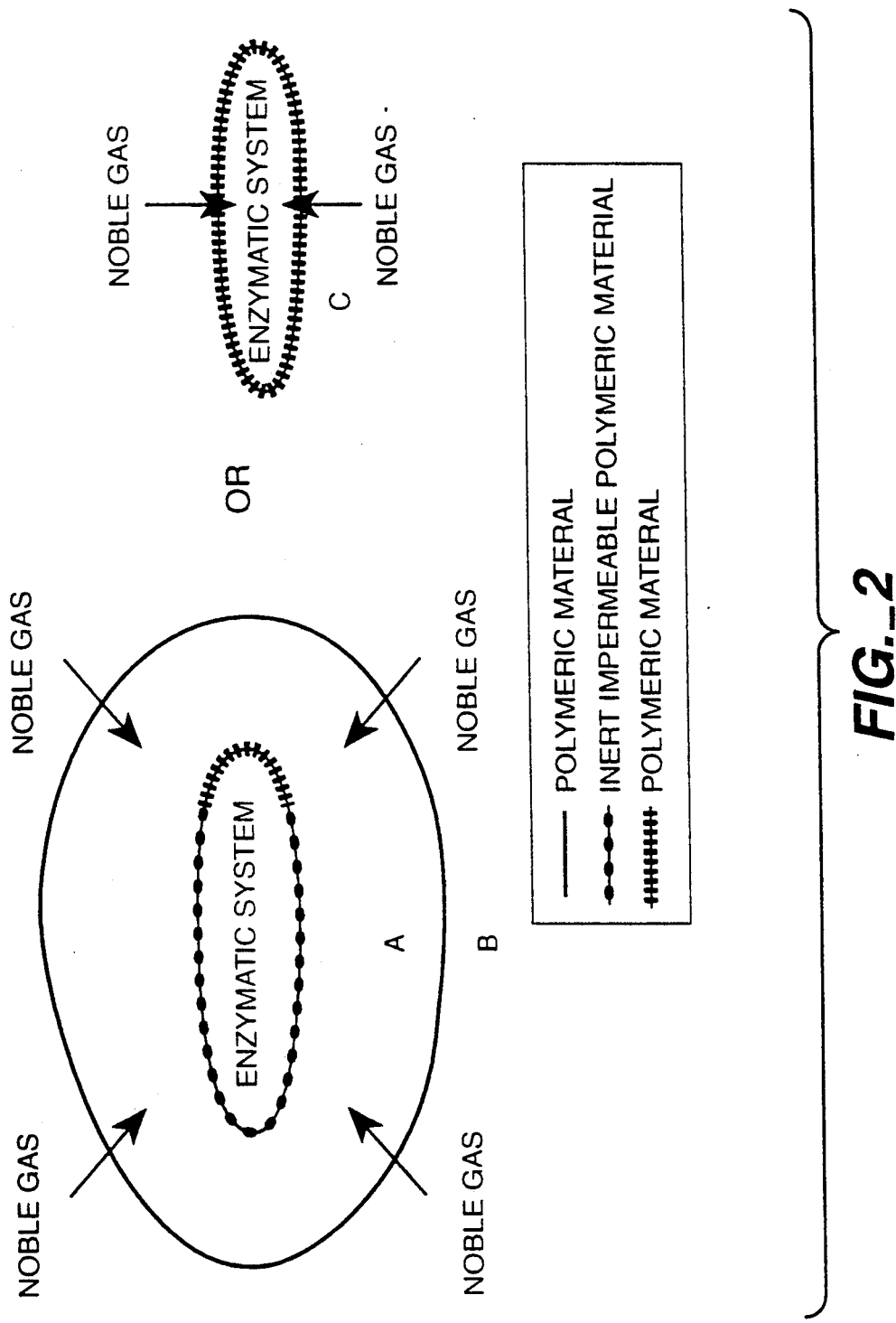
FIG._2

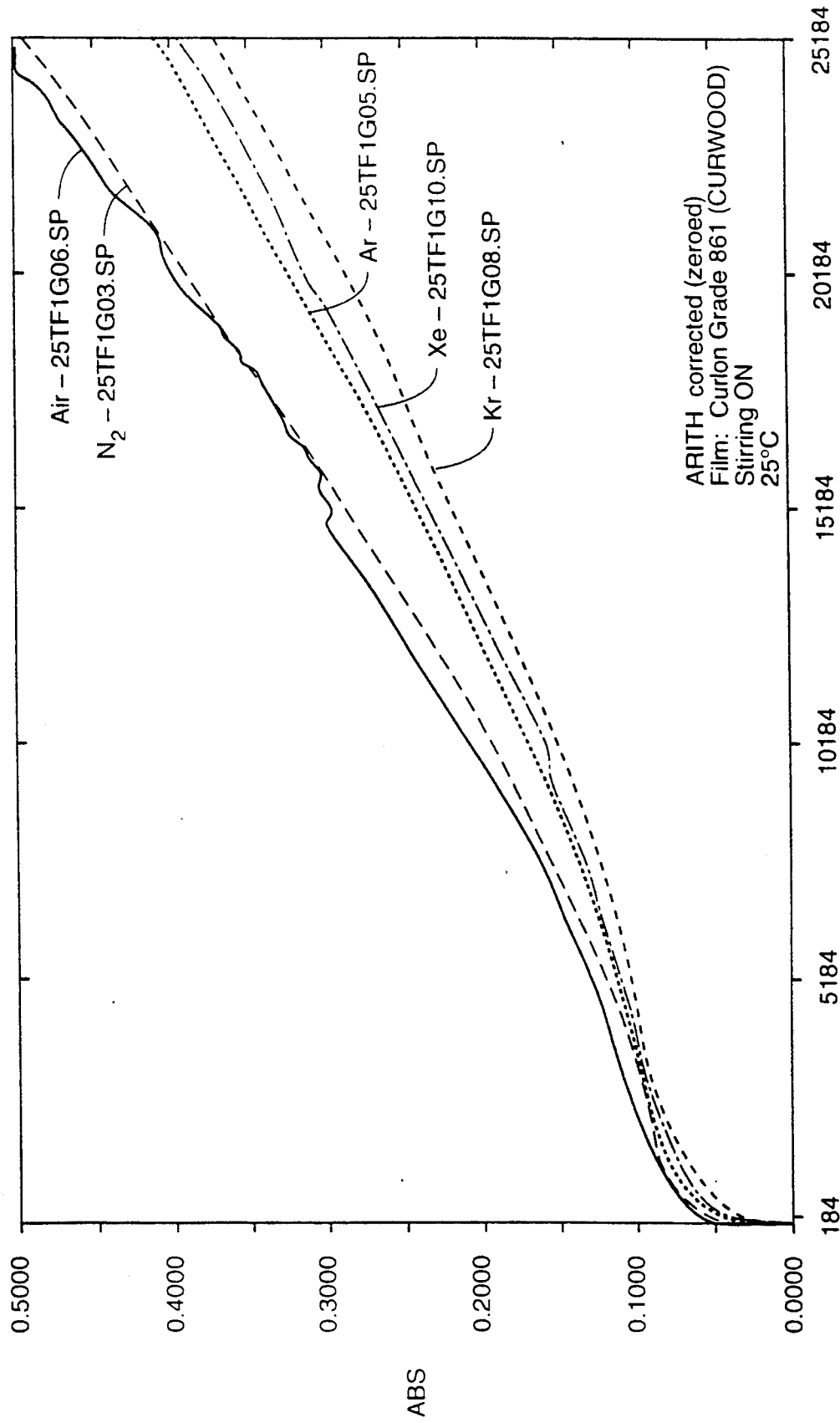
FIG._3

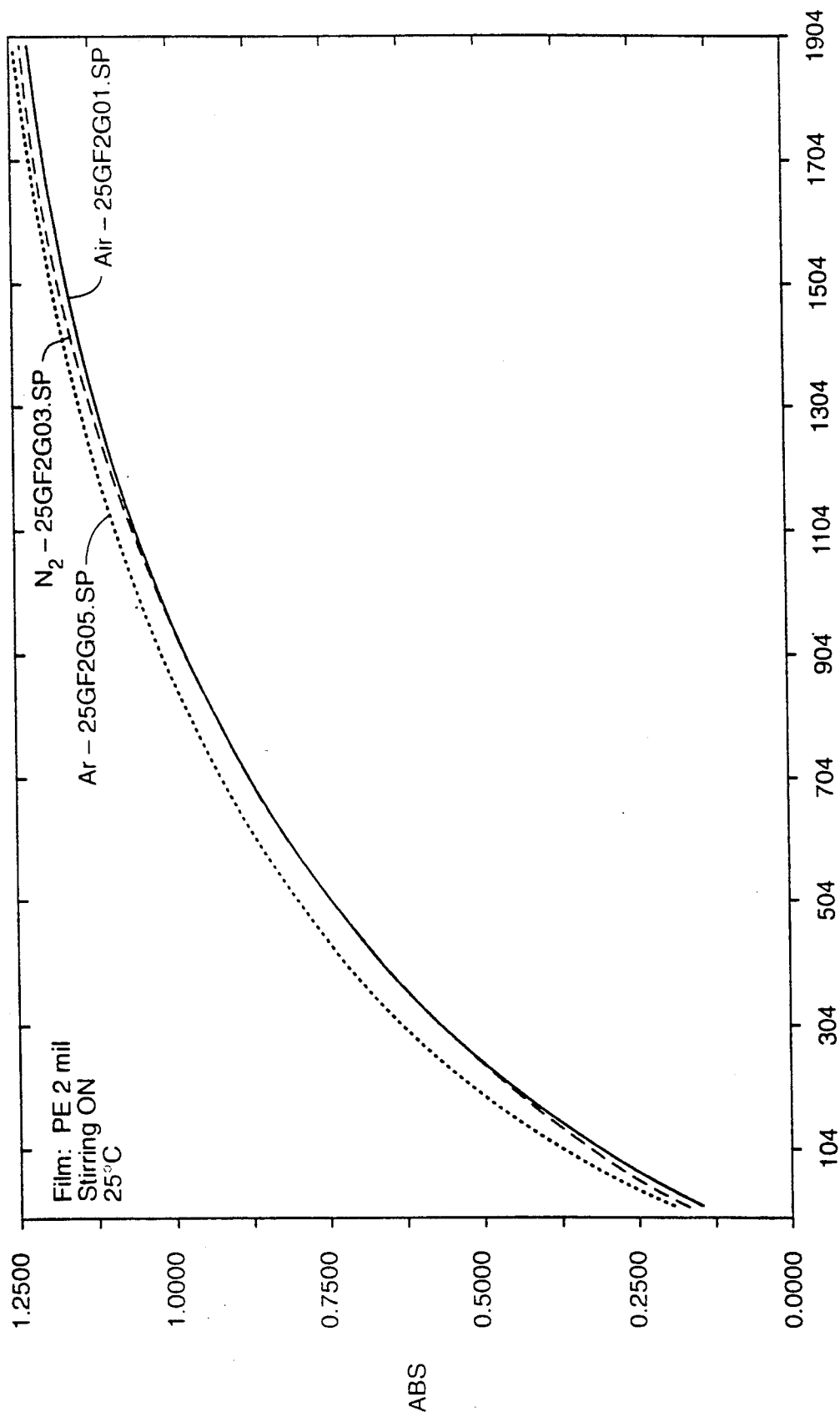
FIG._4

ENZYME-BASED BIOSENSORS FOR DETECTING NOBLE GASES

BACKGROUND OF THE INVENTION

1. Field of the Invention

The present invention relates to enzyme-based biosensors for detecting noble gases.

2. Description of the Background

The ability of the noble gases helium (He), neon (Ne), argon (Ar), krypton (Kr), xenon (Xe) and radon (Ra) to enter into chemical combination with other atoms is extremely limited. Generally, only krypton, xenon and radon have been induced to react with other atoms, which are highly reactive, such as fluorine and oxygen, and the compounds thus formed are explosively unstable. See *Advanced Inorganic Chemistry*, by F. A. Cotton and G. Wilkinson (Wiley, Third Edition). However, while the noble gases are, in general, chemically inert, xenon is known to exhibit certain physiological effects, such as anesthesia. Other physiological effects have also been observed with other inert gases such as nitrogen, which, for example, is known to cause narcosis when used under great pressure in deep-sea diving.

It has been reported in U.S. Pat. No. 3,183,171 to Schreiner that argon and other inert gases can influence the growth rate of fungi and argon is known to improve the preservation of fish or seafood. U.S. Pat. No. 4,946,326 to Schvester, JP 52105232, JP 80002271 and JP 77027699. However, the fundamental lack of understanding of these observations clearly renders such results difficult, if not impossible, to interpret. Moreover, the meaning of such observations is further obscured by the fact that mixtures of many gases, including oxygen, were used in these studies. Further, some of these studies were conducted at hyperbaric pressures and at freezing temperatures. At such high pressures, it is likely that the observed results were caused by pressure damage to cellular components and to the enzymes themselves.

For example, from 1964 to 1966, Schreiner documented the physiological effects of inert gases particularly as related to anesthetic effects and in studies relating to the development of suitable containment atmospheres for deep-sea diving, submarines and spacecraft. The results of this study are summarized in three reports, each entitled: "Technical Report. The Physiological Effects of Argon, Helium and the Rare Gases," prepared for the Office of Naval Research, Department of the Navy. Contract Nonr 4115(00), NR: 102-597. Three later summaries and abstracts of this study were published.

One abstract, "Inert Gas Interactions and Effects on Enzymatically Active Proteins," Fed. Proc. 26:650 (1967), restates the observation that the noble and other inert gases produce physiological effects at elevated partial pressures in intact animals (narcosis) and in microbial and mammalian cell systems (growth inhibition).

A second abstract, "A Possible Molecular Mechanism for the Biological Activity of Chemically Inert Gases," In: Intern. Congr. Physiol. Sci., 23rd, Tokyo, restates the observation that the inert gases exhibit biological activity at various levels of cellular organization at high pressures.

Also, a summary of the general biological effects of the noble gases was published by Schreiner in which the principal results of his earlier research are restated. "General Biological Effects of the Helium-Xenon Series of Elements," Fed Proc. 27:872-878 (1968).

However, in 1969, Behnke et al refuted the major conclusions of Schreiner. Behnke et al concluded that the effects reported earlier by Schreiner are irreproducible and result solely from hydrostatic pressure, i.e., that no effects of noble gases upon enzymes are demonstrable. "Enzyme-Catalyzed Reactions as Influenced by Inert Gases at High Pressures." J. Food Sci. 34: 370-375.

In essence, the studies of Schreiner were based upon the hypothesis that chemically inert gases compete with oxygen molecules for cellular sites and that oxygen displacement depends upon the ratio of oxygen to inert gas concentrations. This hypothesis was never demonstrated as the greatest observed effects (only inhibitory effects were observed) were observed with nitrous oxide and found to be independent of oxygen partial pressure. Moreover, the inhibition observed was only 1.9% inhibition per atmosphere of added nitrous oxide.

In order to refute the earlier work of Schreiner, Behnke et al independently tested the effect of high hydrostatic pressures upon enzymes, and attempted to reproduce the results obtained by Schreiner. Behnke et al found that increasing gas pressure of nitrogen or argon beyond that necessary to observe a slight inhibition of chymotrypsin, invertase and tyrosinase caused no further increase in inhibition, in direct contrast to the finding of Schreiner.

The findings of Behnke et al can be explained by simple initial hydrostatic inhibition, which is released upon stabilization of pressure. Clearly, the findings cannot be explained by the chemical-$O_2$/inert gas interdependence as proposed by Schreiner. Behnke et al concluded that high pressure inert gases inhibit tyrosinase in non-fluid (i.e., gelatin) systems by decreasing oxygen availability, rather than by physically altering the enzyme. This conclusion is in direct contrast to the findings of Schreiner.

In addition to the refutation by Behnke et al, the results reported by Schreiner are difficult, if not impossible, to interpret for other reasons as well.

First, all analyses were performed at very high pressure, and were not controlled for hydrostatic pressure effects.

Second, in many instances, no significant differences were observed between the various noble gases, nor between the noble gases and nitrogen.

Third, knowledge of enzyme mode of action and inhibition was very poor at the time of these studies, as were the purities of enzymes used. It is impossible to be certain that confounding enzyme activities were not present or that measurements were made with a degree of resolution sufficient to rank different gases as to effectiveness. Further, any specific mode of action could only be set forth as an untestable hypothesis.

Fourth, solubility differences between the various gases were not controlled, nor considered in the result.

Fifth, all tests were conducted using high pressures of inert gases superimposed upon 1 atmosphere of air, thus providing inadequate control of oxygen tension.

Sixth, all gas effects reported are only inhibitions.

Seventh, not all of the procedures in the work have been fully described, and may not have been experimentally controlled. Further, long delays after initiation of the enzyme reaction precluded following the entire course of reaction, with resultant loss of the highest readable rates of change.

Eighth, the reported data ranges have high variability based upon a small number of observations, thus precluding significance.

Ninth, the levels of inhibition observed are very small even at high pressures.

Tenth, studies reporting a dependence upon enzyme concentration do not report significant usable figures.

Eleventh, all reports of inhibitory potential of inert gases at low pressures, i.e., <2 atm., are postulated based upon extrapolated lines from high pressure measurements, not actual data.

Finally, it is worthy of reiterating that the results of Behnke et al clearly contradict those reported by Schreiner in several crucial respects, mainly that high pressure effects are small and that hydrostatic effects, which were not controlled by Schreiner, are the primary cause of the incorrect conclusions made in those studies.

Additionally, although it was reported by Sandhoff et al, FEBS Letters, vol. 62, no. 3 (March, 1976) that xenon, nitrous oxide and halothane enhance the activity of particulate sialidase, these results are questionable due to the highly impure enzymes used in this study and are probably due to inhibitory oxidases in the particles.

To summarize the above patents and publications and to mention others related thereto, the following is noted.

Behnke et al (1969), disclose that enzyme-catalyzed reactions are influenced by inert gases at high pressures. J. Food Sci. 34: 370–375.

Schreiner et al (1967), describe inert gas interactions and effects on enzymatically, active proteins. Abstract No. 2209. Fed. Proc. 26:650.

Schreiner, H. R. 1964, Technical Report, describes the physiological effects of argon, helium and the rare gases. Contract Nonr 4115 (00), NR: 102-597. Office of Naval Research, Washington, D.C.

Schreiner, H. R. 1965, Technical Report, describes the physiological effects of argon, helium and the rare gases. Contract Nonr 4115 (00), NR: 102-597. Office of Naval Research, Washington, D.C.

Schreiner, H. R. 1966, Technical Report, describes the physiological effects of argon, helium and the rare gases. Contract Nonr 4115 (00), NR: 102-597. Office of Naval Research, Washington, D.C.

Doebblere, G. F. et al, Fed. Proc. Vol. 26, p. 650 (1967) describes the effect of pressure or of reduced oxygen tension upon several different enzymes using the gases Kr, Xe, $SF_6$, $N_2O$, He, Ne, Ar and $N_2$. All gases were considered equal in their effect.

Colten et al, Undersea Biomed Res. 17 (4), 297–304 (1990) describes the combined effect of helium and oxygen with high pressure upon the enzyme glutamate decarboxylase. Notably, only the hyperbaric inhibitory effect of both helium and oxygen and the chemical inhibitory effect of oxygen was noted.

Nevertheless, at present, it is known that enzyme activities can be inhibited in several ways. For example, many enzymes can be inhibited by specific poisons that may be structurally related to their normal substrates. Alternatively, many different reagents are known to be specific inactivators of target enzymes. These reagents generally cause chemical modification at the active site of the enzyme to induce loss of catalytic activity, active-site-directed irreversible inactivation or affinity labeling. See *Enzymatic Reaction Mechanisms* by C. Walsh (W. H. Freeman & Co., 1979). Alternatively, certain multi-enzyme sequences are known to be regulated by particular enzymes known as regulatory or allosteric enzymes. See Bioenergetics, by A. L. Leninget (Benjamin/Cummings Publishing Co., 1973).

Traditionally used gas sensors include chemical sensors and semiconductor devices. For example, has been developed a chemical gas sensor by using organically modified silicates as gas-sensing substances. The gas sensor consists of thin layers of organically modified silicates coupled to thin film interdigital capacitors (IDC). Changes in the dielectric properties of the modified silicates, which are caused by gases such as $NO_2$ $NH_3$ and $SO_2$ are reflected by a change in the capacitance and conductivity of the capacitor.

U.S. Pat. Nos. 5,085,760, 5,032,248, 4,988,539, 4,792,752, 4,713,646, and 3,719,564 describe electrochemical gas sensors.

U.S. Pat. No. 5,071,770 describes the development of a nitrous oxide electrode which is based upon a chemically specific interaction.

U.S. Pat. No. 4,227,984 describes a gas sensor using an ion transporting membrane.

SU 631812 describes an electrochemical sensor for oxygen that includes a polymer membrane.

JP 53149395 describes an electrochemical sensor for oxygen.

DE 2808165 describes a potentiostatic solid polymer electrolyte gas sensor.

SU 474727 describes a gas detector using a potentiometric sensor.

DE 2237793 describes a gas sensor to measure blood gases involving the use of a composite membrane, with two types of permeability towards interacting and non-interacting gases.

U.S. Pat. No. 5,060,529 describes a semipermeable membrane probe for invasive detection of gases in a sealed package which is amperometric.

All of the sensors described herein are restricted to the detection of chemicals or elements without the application of enzymes.

A second group of sensors are those which are enzyme-based.

Four categories of biosensors can be distinguished (Danilov and Ismailov, 1989; Graham and Moo-Young, 1985):

1. Electrochemical biosensors (oxygen- and ion-selective electrodes with immobilized enzymic membranes)
2. Immunological and bioaffinity (electrodes containing an enzyme or any other protein or an antibody)
3. Optical (fiber-optic bundles with immobilized enzymes)
4. Bioelectronic (based on semiconductors and biological materials)

Enzymes can be immobilized (Gebelein, 1985). Adsorption (ADEw), covalent bonding (CBE), cross-linking (CLE), matrix entrapment (MEE), and membrane encapsulation (EIM) are the methods used to immobilize enzymes (Treyan, 1980).

Enzyme biosensors are enzyme electrodes, wherein one or several enzymes are coupled to an electrochemical sensor that produces a signal proportional to the quantity of substrate consumed or product formed during the catalytic reaction. The enzyme is usually entrapped in an inert membrane matrix which is physically conjugated to the sensor. The performance of the biosensor (linear response, sensitivity, response time, operational stability) is directly linked to the characteristics of the enzyme membrane (porosity, thickness, stability).

To cite some examples of enzyme electrodes: acetylcholine and urea can be determined respectively by means of an acetylcholine esterase electrode (detection of a decrease in pH) and of an urease electrode (detection of an increase in pH); penicillin G can be determined by using a penicillinase electrode; glucose levels can be measured by a glucose oxidase electrode.

U.S. Pat. No. 4,721,677 describes an enzyme-based sensor for measuring glucose levels, which contains an oxygen reservoir, from which the oxygen is fed to the enzyme through an oxygen permeable membrane.

U.S. Pat. No. 5,120,420 describes the assembly of enzyme/electron acceptor based biosensors.

U.S. Pat. No. 4,885,077 describes a membrane enzyme combination sensor assembly.

A third group of sensors are those which are gas biosensors.

Notably, no enzyme-based sensors for noble gases have been developed.

Development of gas biosensors is based on biological or enzymatic materials. Enzymes are of interest because of their substrate specificity, which confers a higher selectivity to the gas biosensors in comparison to the traditional chemical sensors.

The following enzyme-based gas sensors have been developed.

Notably, several diffusion dependent enzyme badges have been developed to measure toxic gaseous compounds in the workplace atmosphere (hydrogen peroxide, formaldehyde, acetaldehyde, and ethanol). The gaseous substrate molecules reach the badge surface by diffusion, where the enzyme is located, and are converted. The formation of colored compounds due to the combined chemical reagent allows the following of the enzymatic conversion. Color comparison permits to determine the concentration of the gaseous compound.

However no enzyme-based sensors for noble gases have been described. This is because all previous sensors have depended upon chemical reactions of the gas with the sensors, and noble gases are not capable of such reactions.

Thus, a need exists for a means by which gases may be detected.

SUMMARY OF THE INVENTION

Accordingly, it is an object of the present invention to provide a method of detecting at least one noble gas.

It is, moreover, an object of this invention to provide also an apparatus for detecting one or more noble gases.

Accordingly, the above objects and others are provided by a method of detecting at least one noble gas, which entails permeating the at least one noble gas through a semi-permeable membrane, allowing said permeating noble gas to contact an enzyme, the activity of which is changed by the noble gas, and detecting the change in enzyme activity.

BRIEF DESCRIPTION OF THE DRAWINGS

FIG. 1 illustrates a two-chambered diffusion cell for use in accordance with the present invention.

FIG. 2 illustrates a gas biosensor in accordance with the present invention.

FIG. 3 illustrates the results of a gas biosensor experiment using Air, $N_2$, Ar, Kr or Xe in the upper chamber of the biosensor, which demonstrates the effect of the present invention.

FIG. 4 illustrates the results of a gas biosensor experiment using Air, $N_2$ or Ar in the upper chamber of the biosensor, which demonstrates the effect of the present invention.

DETAILED DESCRIPTION THE PREFERRED EMBODIMENTS

In accordance with the present invention, a method is provided for detecting noble gases by coupling an enzymatic system to one or more polymeric membranes of determined diffusive properties. The construction of such biosensing systems is the essence of the present invention. They allow the detection of the pure gases xenon, krypton, argon, and neon alone or in mixtures, or in mixtures with other gases.

Noble gas levels are presently detected through sophisticated analytical hardware such as GC/MS. The present invention will have broad utility in applications wherein a rapid assessment of noble gas levels is desirable, such as in lasers, or where noble gas leaks have to be detected or where invasive sampling is undesirable such as in the case of gas packaging, or wherever differential detection of quantitative levels of noble gases is desired.

A device and a method have been designed wherein noble gases are detected alone or in mixtures, or with other gases, by their differential permeability through a semi-permeable polymeric membrane and by their differential ability to inhibit or enhance enzyme activity, where this activity is coupled to a detectable component, for example a colorigenic reaction.

The apparatus of the present invention may be generally described as follows.

The present device can generally consist of a container of any shape or form (tubular, spherical, cylindrical for example), made of an inert material, such as glass, a high barrier type of polymer, or stainless steel, or another metal, or plastic, or a composite assembly, through which the gas of interest cannot diffuse, with one or more apertures covered with a polymeric material permitting diffusion of the gas to be measured. Included within the container is a reaction system consisting of an enzyme and a substrate, which can be inhibited or enhanced by the gas to be measured in a manner different from other gases with which it may be admixed. Also the reaction system will possess a measurable component, such as a visually colorigenic component for example, by which the progress of the reaction may be monitored.

For example, the biosensor herein described may comprise a UV/VIS 1 cm-path cuvette topped with a polymeric film, which diffusive properties are adequate for the enzyme complex/gas interaction. This device is illustrated in FIG. 1, wherein a double-chambered assembly is usefully employed.

The chamber containing the biochemical reactant system can be connected to any noble gas containing system, wherein the level of these gases need to be assessed.

The biosensor herein described can consist solely of the polymeric film. It can be for example a small sealed polymeric bag of any shape or form, that will contain the enzymatic reactants and be, for example, impermeable to water and, thus, be useful in liquid or wet environments, such as food packages. This device is illustrated in FIG. 2.

Also illustrated in FIG. 2 is a device which has both an impermeable solid support component as well as a permeable component.

The enzymatic system can either be liquid or solid. A solid support on which the enzymatic system has been immobilized can be substituted for the chamber system.

Output detection of these biosensing devices can be by means of colorimetry, either gain or loss of color, or direct reading by ultra violet/visible spectrophotometry or fluorescence.

The gas permeation module can be separated from the biochemical one in time or space, but the essence of this invention consists in the use of both modules.

In modified atmosphere packaging of food products, the polymeric material can be chosen to be biocompatible with edible products.

The direct or indirect potentiation or inhibition of enzyme activity by contact with noble gases, in combination with the differential diffusion properties of these gases through a semipermeable polymeric membrane is used in order to detect the pure gases xenon, krypton, argon, and neon alone or in mixtures, or in mixtures with other gases, in the present invention.

With an appropriate choice of an enzyme/film tandem, the present biosensors can detect the pure gases argon, neon, krypton and xenon alone. As an example a tyrosinase (EC 1.14.18.1) reaction system containing a colorigenic substrate restrained by a coextruded polymeric material with differential diffusive properties for noble gases will exhibit different rates of absorbance increase at 305 nm for argon, krypton and xenon in comparison to air and nitrogen.

These biosensors can detect any mixture of noble or other gases such as $CO_2$, $N_2$ or $O_2$ or even air. A standard calibration curve has to be established prior to analysis, to determine the enzymatic response to this particular gaseous mixture in the diffusive conditions set by the choice of the polymeric membrane.

Some other gases, such as oxygen or carbon dioxide, when present in the gas mixture to be assessed, can react or be reacted by the enzymatic system, which is not the case for noble gases. In this instance, oxygen or carbon dioxide can be a substrate or cosubstrate of the enzyme. As an example oxygen is a co-substrate in the oxidation of L-tyrosine by tyrosinase.

Sensitivity limits of these biosensing devices can be assessed by establishing a calibration curve.

The device described above can be used in situ, or a gas collector can be engineered and placed at a later time in contact with the enzyme.

These biosensors can be operational in various types of media, water or oil, as long as an hydrophobic or oleophobic film with the adequate diffusive properties has been selected.

One output of these biosensing systems can consist of a visible positive (appearing) or negative (disappearing) change in color.

These biosensors are operational in any temperature or pH range suitable for a readable enzymatic activity. Since the enzymatic response differs depending on the temperature and pH conditions, a standard calibration curve has to be established previously, to determine the enzymatic response in the given conditions.

These biosensors are operational in any pressure range that will not cause tearing of the polymeric material so long as diffusion of noble gas across the film is not prevented.

Further, in accordance with a preferred aspect of the present invention, a method is provided for detecting at least one noble gas through a semi-permeable membrane, which entails injecting a gas or a gas mixture into a reaction or detection space where the noble gas contacts the enzyme, the gas or gas mixture containing an element selected from the group consisting of argon, krypton, xenon and neon and any mixture thereof; substantially saturating the reaction or detection space with the gas or gas mixture; maintaining said saturation substantially throughout the volume of the reaction or detection space, and for a time, sufficient to allow for detection of the noble gas.

It has been surprisingly discovered that by substantially saturating the reaction space around the enzyme with the noble gas being detected, which is selected from the group consisting of argon, krypton, xenon and neon and a mixture thereof, it is possible to substantially improve the effect of the present invention, particularly when said saturation or substantial saturation is maintained throughout the volume of the reaction space and during substantially all the time required for detection of the noble gas.

The term "substantially saturate" means that it is not necessary to completely and/or constantly saturate the reaction space or medium with said gas or gas mixture (i.e., having the maximum amount of gas solubilized in said reaction space or medium). Usually, it is considered necessary to saturate said reaction space on medium to more than 50% of its (full) saturation level and preferably more than 70%, while 80% or more is considered the most adequate level of saturation of the reaction space or medium. Of course, supersaturation is also possible. This means that if during reaction of the enzyme with the noble gas if the reaction space or medium remains generally substantially saturated, results according to the invention are usually obtained. While it is believed that it is important that the entire volume of the reaction space or medium be saturated or substantially saturated with one of the above gas or a mixture thereof, it is quite possible to obtain the results according to the invention if a part of the reaction space or medium is not saturated during preferably a limited period of time or is less saturated or substantially saturated than other portions of the reaction space or medium.

While at least one of the above gases must be present in order to obtain the benefits of the invention, said gases can be diluted with some other gases, in order to keep for example the invention economically valuable. Said diluent gases are preferably selected from the group comprising nitrogen, oxygen, nitrous oxide, air, helium or carbon dioxide. In case of an oxygen-containing gas or another reactive gas such as carbon dioxide, their degradative properties are such that these properties will mask the effect of noble gases, certainly in mixtures where they comprise 50% vol. or more and possibly 30% vol. or more. When those mixes comprise 0% to 10% vol. of these other gases, the noble gases referred to above are still extremely effective, while between 10% vol. and 20% vol. they are usually still effective, depending on the type of gases and conditions, which might be easily determined by the man skilled in the art.

In case of nitrogen and/or helium gas, the effect of noble gases consisting of Ar, Ne, Kr, Xe in the mixture is linearly proportional to its concentration in the mixture, which evidences that nitrogen and/or helium have no effect on substantially preventing influencing the rate or yield of enzymatic reactions. The mixture of noble gas and nitrogen and/or helium can thus comprise any amount (% volume) of nitrogen and/or helium:

however, in practice, the lesser the proportion of noble gas selected from the group consisting of Ar, Ne, Kr and Xe, the larger the time required to achieve saturation or substantial saturation of the reaction space.

Among the active gases (Ar, Kr, Xe, and Ne), it is preferred to use argon because it is cheaper than the other active gases. However, mixtures of argon and/or krypton and/or xenon are at least as effective as argon alone. has also been unexpectedly found that mixtures comprising between 90 to 99% vol. argon and 1 to 10% Xe and/or Kr are usually the most effective as exemplified in the further examples (whether or not they are diluted with nitrogen, helium, or nitrous oxide). The difference in effect between the active gases defined hereabove and nitrogen have been also evidenced by the fact that mixtures of argon and oxygen or carbon dioxide have a similar (while decreased) effect than argon alone, while nitrogen mixed with oxygen or carbon dioxide evidenced no protective or preservative effect compared to oxygen or carbon dioxide alone.

Generally speaking, Xe is the most efficient gas according to the invention, followed by Kr, Ar and Ne. Among the suitable mixes, either pure or diluted with $N_2$, He, $N_2O$ (or even air, oxygen or a small amount of hydrogen) are the Ne/He mix comprising about 50% vol. of each, and the Kr/Xe mix comprising about 5-10% vol. Xe and about 90-95% vol. Kr, with a small amount of argon and/or oxygen (less than 2% vol.) or nitrogen (less than 1% vol.).

The temperatures at which the invention is carried out is usually between about 0° C. to 60° C., and preferably about 10° C. and 30° C.

The injection of the gas or gas mixture into the wine and/or into the container, e.g. by sparging is usually done at about 1 atmosphere but is still quite operable at 2 or 3 atmospheres, while saturation is increased at higher pressures. The pressure of the reaction space in the container shall be, in any case, preferably lower than 10 atmospheres and it is usually acceptable to maintain it lower than 3 atmospheres.

There are a variety of standard methods available for the detection, qualitative and quantitative measurement of gases, and several are especially well suited for the determination of degree of saturation of noble gases into liquid samples.

Samples generally are completely evacuated as a control for zero % saturation. Such samples may then be completely saturated by contact with noble gases such that no additional noble gas will disappear from a reservoir in contact with the sample. Such saturated samples may then have their gas content driven off by trapped evacuation or by increase in temperature, and said gas sample identified quantitatively and qualitatively. Analysis is of trapped gases, reservoir gases, or some other headspace of gases, not directly of the sample.

Direct sample analysis methods are available, and include comprehensive GC/MS analysis, or by mass or thermal conductance or GC analysis and comparison with calibrated standards.

The simplest method is GC/MS (gas chromatography/mass spectrometry), which directly determines gas compositions. By preparing a standard absorption curve into a given sample for a series of gases and mixtures, one can accurately determine the degree of saturation at any point in time.

GC/MS is applied to the gas itself, as in the headspace above a sample. The technique may be used either to determine the composition and quantity of gas or mixture being released from a sample, or conversely the composition and quantity of a gas or mixture being absorbed by a sample by following the disappearance of the gas.

Appropriate GC/MS methods include, for example, the use of a 5 Angstrom porous layer open tubular molecular sieve capillary glass column of 0.32 mm diameter and 25 meter length to achieve separation, isothermally e.g. at 75° C. or with any of several temperature ramping programs optimized for a given gas or mixture e.g. from 35°-250° C. wherein ultra-high purity helium or hydrogen carrier gas is used at e.g. 1.0 cc/min flow rate, and gases are detected based upon their ionicity and quantitative presence in the sample, and characterized by their unique mass spectra.

Appropriate experimental conditions might include, for example, completely evacuating a given sample under vacuum to remove all absorbed and dissolved gases, then adding a gas. or mixture to the sample and measuring a) the rate of uptake of each component as disappearance from the added gas, and/or b) the final composition of the gas headspace after equilibration. Both measurements are made by GC/MS, and either method can be used in both batch and continuous modes of operation.

A simplification of this analysis entails the use of a GC only, with a thermal conductivity detector, wherein adequate knowledge of the gas saturation process and preparation of calibration curves have been made such that quantification and characterization of gases and mixtures can be accomplished without mass spectral analysis. Such instruments are relatively inexpensive and portable.

A further simplification would depend solely upon measurement of the mass change in the sample upon uptake of various gases or mixtures, which depends upon the use of standard curves or absorption data available from the literature.

An alternate method for such mass measurements is thermogravimetric analysis, which is highly precise, wherein a sample is saturated with gas and mass changes are correlated to thermal change.

Having generally described the present invention, reference will now be made to certain examples which are provided solely for purposes of illustration and are not intended to be limitative.

Biosensor diffusion cells are built for use in a UV/VIS spectrophotometer, which permits the assay of noble gases through their effect on noble gas sensitive biochemical reactions.

Construction consists of coupling two 1-cm lightpath UV grade methacrylate covets with a ring of 100% silicone rubber (General Purpose Sealant, Dow Corning) applied on their outside rim. Before sealing with silicone, a 1-$cm^2$ square of a polymeric film of known permeabilities to the different gases is placed between the two cuvettes. Holes have been previously drilled in each covet (drill bit 7/64") to receive a septum (d=3 mm; h=8 mm; Supelco No. 3-3301M). 100% silicone rubber was applied around the septa to avoid possible leaks. A diagram of this diffusion cell is given in FIG. 1.

The enzymatic reactions are followed with a Perkin-Elmer Lambda 6 UV/VIS spectrophotometer, temperature controlled, connected to an IBM PS/2 30 personal computer. The IBM is loaded with a Perkin-Elmer (PECSS) software package to record and view spectra.

The data gathered during the gas biosensor runs are compared with the gas permeability results that are obtained by the reference method: gas chromatography coupled to mass spectrometry. The equipment consists of a Hewlett-Packard 5890 SERIES II Gas Chromatograph and a Hewlett-Packard 5971A Mass Spectrometer connected to an HP Vectra QS/20 personal computer. The HP is loaded with an HP G1030A MS ChemStation software package to acquire and analyze data. Chromatography is performed on a 25 m×0.32 mm Molecular Sieve (Molsieve) 5 Å PLOT column (CHROMPACK Inc., NJ), using helium as a carrier gas.

Solution preparation: optimized W/V solutions are prepared by diluting the enzyme (units/ml) and the substrate (μg/ml) in appropriate buffer (optimized pH and molarity for enzymes). The solutions are used for diffusion experiments at once to avoid loss of activity. Various enzyme and substrate concentrations may be employed. Physical parameters are varied as required.

The first detailed example of the invention consists of testing of an oxido-reductase-based biosensor.

EXAMPLE 1

Detailed Protocol

BIOSENSORS/NOBLE GAS ASSAYS

I. DIFFUSION CELL DESIGN

To obtain a uniform color development in chamber 2, a magnetic spinner (Microbar 7 mm×2 mm) is added.

II. PACKAGING MATERIAL ASSAYED

The following polymeric film is assayed:

| Commercial Name or other | Manufacturer or other | Film Type | Polymers | Gauge (mil) |
|---|---|---|---|---|
| Curlon Grade 861 | CURWOOD | Coex. | Nylon PVDC PE | 3 |

III. ANALYTICAL EQUIPMENT

The enzymatic reactions are followed with a Perkin-Elmer Lambda 6 UV/VIS spectrophotometer.

The data gathered during the gas biosensors runs are compared with the gas permeability results that are obtained by the reference method: gas chromatography coupled to mass spectrometry.

GC columns set up:
25 m×0.32 mm Molecular Sieve (Molsieve) 5 Å PLOT column (CHROMPACK Inc., NJ)
Carrier gas: He (15 psi column headpressure)

IV. BIOCHEMICAL REACTION INVOLVED

The enzymatic reaction involved in the assay procedure is the following:
Tyrosinase/L-Tyrosine monitored at 305 nm

V. BIOSENSOR ASSAY

1. Biochemical Sensor a. Reagents

Enzyme: Tyrosinase (SIGMA No. T-7755) (Monophenol monooxygenase; Polyphenol oxidase; Catechol oxidase; Monophenol, dihydroxyphenylalanine: oxygen oxidoreductase; From Mushroom Tyrosinase Unit Definition One unit will cause an increase in $A_{200}$ of 0.001 per min at pH 6.5 at 25° C. in 3 mL reaction mix containing L-tyrosine. Tyrosinase activity: 3870 U/mg solid 7.1 mg solid > 27,440 Units Stored desiccated below 0° C.

Substrate: L-Tyrosine (SIGMA No. T-3754) L-3-[4-Hydroxyphenyl ]alanine Free Base (pfs) Crystalline Anhydrous Mol. Wt. 181.2 Stored at room temperature (25° C.)

b. Solution Preparation

Soln A: Sodium phosphate buffer pH 6.6 at 25° C.
1 L Deionized water $$141.96 \times 0.2 \times 187.5 \times 1/1000 = 5.3 \text{ g } Na_2HPO_4$$

$$119.96 \times 0.2 \times 312.5 \times 1/1000 = 7.5 \text{ g } Na_2HPO_4$$

Stored in refrigerator in a Nalgene bottle (0°–5° C.).

Soln B: Tyrosinase solution in Na Phos. buffer (228 U/ml)

14.2 mg T-7755 diluted to 240 mL Na Phos. buffer pH 6.6 at 25° C. 100 ml of solution is stored in a 160 cc glass serum vial, wrapped in aluminum foil (to prevent light degradation), in refrigerator (0°–5° C.). The serum vial is capped with a rubber septum and crimp-sealed with an aluminum cap to be gas-tight. Additionally the serum vial is purged by bubbling on-line $N_2$ through (10 psi delivery pressure) for 7 min and left under a slight positive pressure.

Soln C: 50 μg/mL L-Tyrosine solution in Na Phos. buffer 10 mg T-3754 diluted to 200 ml Na Phos. buffer pH 6.6 at 25° C.

100 ml of solution is stored in a 160 cc glass serum vial, wrapped in aluminum foil (to prevent light degradation), in refrigerator (0°–5° C.). The serum vial is capped with a rubber septum and crimp-sealed with an aluminum cap to be gas-tight. Additionally the serum vial is purged by bubbling on-line $N_2$ through (10 psi delivery pressure) for 7 min and left under a slight positive pressure.

c. Run preparation

For each diffusion cell studied, the procedure consists of the following:
Both chambers are initially under air.
Chamber 1 (upper) is flushed for 2 min with 100% nitrogen (very low flow to prevent tearing of the polymeric film: line delivery pressure <5 psi) at ambient temperature (25° C.), using 22G1½ needles (small gauge to reduce risks of leakage through holes in septa).
Chamber 2 (lower) is flushed in the same way as chamber 1.
Chamber 2 is then filled with 2.0 ml of $N_2$-saturated solution C, by means of a 3 cc syringe (previously purged with $N_2$).
Additionally an acrylic covet is filled with 2.0 ml of solution A and 0.5 ml of solution B to serve as a reference.

d. Spectrophotometric runs

The settings are the following:

| Slit | 1 nm |
|---|---|
| Speed | 1500 nm/min |
| CPRG (Cell programmer) | 5 cells |
| Wavelength | 305 nm |
| Absorbance mode (ABS) | |
| Temperature | 25° C. |

| -continued | |
|---|---|
| Data points | 1575 |
| Time intervals | 16 s (==>7 hr run) |
| File directory | C: PECSS CSSDATA |

Two runs are conducted, one on each spectrophotometer:

Spectro 1:
Cell 1: Air 1
Cell 2: empty
Cell 3: $N_2+++$
Cell 4: empty
Cell 5: Ar Spectro 2:
Cell 1: Air 2
Cell 2: empty
Cell 3: Kr
Cell 4: empty
Cell 5: Xe Blanks: 2 mL Soln A+0.5 mL Soln B
Sample: 2 ml Soln C+0.5 ml Soln B
Filenames:
25TF1GO1.SP Air 1
25TF1GO3.SP $N_2$
25TF1GO5.SP Ar
25TF1GO6.SP Air 2
25TF1GO8.SP Kr
25TF1G1O.SP Xe
(Keycode: 25° C.; Tyrosinase; Film 1; Gas x)

Before the spectrophotometric run, 20 cc of the appropriate gas (Air, $N_2$, Ar, Kr, Xe) is passed through chamber 1 of each of the 3 diffusion cells simultaneously, by means of a 30 cc syringe.

Following immediately, the run starting time $t_0$ is given by the simultaneous injections of 0.5 ml of $N_2$-saturated-solution B in chamber 2 of each diffusion cell. The 1 cc syringes used for sampling the 0.5 ml are previously purged with $N_2$.

2. GC/MS Diffusion data a. Procedure

As in the preparation of the spectrophotometric runs, the procedure consists of the following for each diffusion cell studied:
Both chambers are initially under air.
Chamber 1 (upper) is flushed for 2 rain with 100% nitrogen (very low flow to prevent tearing of the polymeric fim: line delivery pressure <5 psi) at ambient temperature, (25 ° C.), using 22G1½ needles (small gauge to reduce risks of leakage through holes in septa).
Chamber 2 (lower) is flushed in the same way as chamber 1.

For each diffusion cell, the starting time to of the diffusion study is given by the flushing through of 20 cc of the appropriate gas (Air, $N_2$, At, Kr, Xe) in chamber 1 (using 30 cc syringes).

The change in relative gas concentration in both chambers is then monitored by taking 10 μl samples every day for 5 days and injecting them on the GC/MS.

b. GC/MS method

A GC/MS method is set up and stored as C:CHEMP-CMETHODSCEB006.M, appended.

c. Results

The autointegration results giving raw areas and area percents for each gas are transferred to a LOTUS 123 Release 3.1 data matrix.

A second data matrix is generated presenting the GC/MS data corrected for ionicity (relative to xenon). The results for a simple run are given in FIG. 3.

EXAMPLE 2

The second detailed example of the invention consists of the demonstration of a hydrolase-based biosensor.
Detailed Protocol:

BIOSENSOR/NOBLE GAS ASSAYS

I. DIFFUSION CELL DESIGN

To obtain a uniform color development in chamber 2, a magnetic spinner (Microbar 7 mm×2 mm) is added.

II. PACKAGING MATERIAL ASSAYED

The following polymeric film is assayed:

| Commercial Name/ or other | Manufacturer or other | Film Type | Polymers | Gauge (mil) |
|---|---|---|---|---|
| Polyethylene Liner grade | AARGUS POLYBAG CO. | Monolayer | PE | 2 |

III. ANALYTICAL EQUIPMENT

The enzymatic reactions are followed with a Perkin-Elmer Lambda 6 UV/VIS spectrophotometer.

The data gathered during the gas biosensors runs are compared with the gas-permeability results that are obtained by the reference method: gas chromatography coupled to mass spectrometry.
GC columns set up:
25 n×0.32 mm Molecular Sieve (Molsieve) 5 Å PLOT column (CHROMPACK Inc., NJ)
Carrier gas: He (15 psi column headpressure)

IV. BIOCHEMICAL REACTION INVOLVED

The enzymatic reactions involved in the assay procedure is the following: β-D-Glucosidase/p-Nitrophenyl-β-D-Glucopyranoside monitored at 400 nm

V. BIOSENSOR ASSAY

1. Biochemical Sensor a. Reagents
Enzyme: β-D-Glucosidase (SIGMA No. G-4511) (Emulsin; β-D-Glucoside glucohydrolase From Almonds Unit Definition One unit will liberate 1.0 μmole of glucose from salicin per min at pH 5.0 at 37° C. Activity: 22 U/mg solid 12 mg solid >264 Units Stored desiccated at 0°-5° C.
Substrate: p-Nitrophenyl-β-D-Glucopyranoside (SIGMA No. N-7006)
Crystalline
Contains 2.4% solvent
Anhydrous Mo 1. Wt. 301.3
Stored desiccated below 0° C.

b. Solution Preparation

Soln D: Sodium phosphate buffer pH 6.8 at 25° C.:
2 L Deionized water
$2\times141.96\times0.2\times245\times1/1000=13.91$ g $Na_2HPO_4$ $2 \times 119.96 \times 0.2 \times 255 \times 1/1000 = 12.20$ g NaH$_2$PO$_4$ Stored in refrigerator in a Nalgene bottle (0°–5° C.).

Soln E: 100 µg/mL β-D-Glucopyranoside solution in Na Phos. buffer 25 mg N-7006 diluted to 250 ml Na Phos. buffer pH 6.8 at 25° C.

100 ml of solution is stored in a 160 cc glass serum vial, wrapped in aluminum foil (to prevent light degradation), in refrigerator (0°–5° C.). The serum vial is capped with a rubber septum and crimp-sealed with an aluminum cap to be gas-tight. Additionally the serum vial is purged by bubbling on-line N$_2$ through (10 psi delivery pressure) for 7 min and left under a slight positive pressure.

Soln F: B-D-Glucosidase solution in Na Phos. buffer pH 6.8 (25° C.) (2.18 Units/ml)

24 mg G-4511 diluted to 242 mL Na Phos. buffer pH 6.8 at 25° C.

100 ml of solution is stored in a 160 cc glass serum vial, wrapped in aluminum foil (to prevent light degradation), in refrigerator (0°–5° C.). The serum vial is capped with a rubber septum and crimp-sealed with an aluminum cap to be gas-tight. Additionally the serum vial is purged by bubbling on-line N$_2$ through (10 psi delivery pressure) for 7 min and left under a slight positive pressure.

c. Run preparation

For each diffusion cell studied, the procedure consists of the following:

Both chambers are initially under air.

Chamber 1 (upper) is flushed for 2 min with 100% nitrogen (very low flow to prevent tearing of the polymeric rim: line delivery pressure <5 psi) at ambient temperature (25° C.), using 22G1½ needles (small gauge to reduce risks of leakage through holes in septa).

Chamber 2 (lower) is flushed in the same way as chamber 1.

Chamber 2 is then filled with 2.0 ml of N$_2$-saturated solution E, by means of a 3 cc syringe (previously purged with N$_2$).

Additionally an acrylic cuvette is filled with 2.0 ml of solution D and 0.5 ml of solution F to serve as a reference.

d. Spectrophotometric runs

The settings are the following:

| | |
|---|---|
| Slit | 1 nm |
| Speed | 1500 nm/min |
| CPRG (Cell programmer) | 5 cells |
| Wavelength | 400 nm |
| Absorbance mode (ABS) | |
| Temperature | 25° C. |
| Data points | 1575 |
| Time intervals 16 s (= = >7 hr run) | |
| File directory | C: PECSS CSSDATA |

Two runs are conducted, one on each spectrophotometer:

Spectro 1:
  Cell 1: Air 1
  Cell 2: empty
  Cell 3: N$_2$
  Cell 4: empty
  Cell 5: Ar
Spectro 2:
  Cell 1: Air 2
  Cell 2: empty
  Cell 3: Kr
  Cell 4: empty
  Cell 5: Xe
    Blanks: 2 mL Soln D+0.5 mL Soln F
    Sample: 2 ml Soln E+0.5 ml Soln F
    Filenames:
    25GF2GO1.SP Air 1
    25GF2GO3.SP N$_2$
    25GF2GO5.SP Ar
    25GF2GOG.SP Air 2
    25GF2GO8.SP Kr
    25GF2G1O.SP Xe (Keycode: 25° C.; Glucosidase; Film 2; Gas x)

Before the spectrophotometric run, 20 cc of the appropriate gas (Air, N$_2$, Ar, Kr, Xe) is passed through chamber 1 of each of the 3 diffusion cells simultaneously, by means of a 30 cc syringe.

Following immediately, the run starting time $t_0$ is given by the simultaneous injections of 0.5 ml of N$_2$-saturated solution F in chamber 2 of each diffusion cell. The 1 cc syringes used for sampling the 0.5 ml are previously purged with N$_2$.

2. GC/MS Diffusion data a. Procedure

As in the preparation of the spectrophotometric runs, the procedure consists of the following for each diffusion cell studied:

Both chambers are initially under air.

Chamber 1 (upper) is flushed for 2 min with 100% nitrogen (very low flow to prevent tearing of the polymeric rim: line delivery pressure <5 psi) at ambient temperature (25° C.), using 22G1½ needles (small gauge to reduce risks of leakage through holes in septa).

Chamber 2 (lower) is flushed in the same way as chamber 1.

For each diffusion cell, the starting time $t_0$ of the diffusion study is given by the flushing through of 20 cc of the appropriate gas (Air, N$_2$, Ar, Kr, Xe) in chamber 1 (using 30 cc syringes).

The change in relative gas concentration in both chambers is then monitored by taking 10 gl samples every day for 5 days and injecting them on the GC/MS.

b. GC/MS method

A GC/MS method is set up and stored as C:CHEMP-CMETHODSCEB006.M.

c. Results

The autointegration results giving raw areas and area percents for each gas are transferred to a LOTUS 123 Release 3.1 data matrix.

A second data matrix is generated presenting the GC/MS data corrected for ionicity (relative to xenon).

The results for a simple run are given in FIG. 4.

EXAMPLE 3

The above mentioned oxido-reductase system (tyrosinase/L-tyrosine) is placed inside a 3 cc bag by heat-sealing of the polymeric film used in protocol described above (Curlon Grade 861, Curwood).

The 3 cc bag is placed into a series of packages containing food products under different gas mixtures, which include neon, argon, krypton, xenon, oxygen, nitrogen and carbon dioxide. The relative rate of changing color of the device, that is the development of a pink-brown color, is monitored over time.

A similar series is run, but after holes have been punctured in the packages to simulate leaks. The rate of changing color is then monitored. Thus we have made a leak detection system.

In the same manner, the exchange of gases through the film of the packages and the change in respiration of fresh horticultural commodities can also be monitored. For example, in the case of vegetables packaged under 100% Ar, 100% $N_2$ and Ar:$O_2$, by adding to the packages a biosensing bag made of a polymeric membrane permeable to noble gases, it can be seen that the biosensing device placed into the package under 100% Ar turns color more slowly than the one placed into the $N_2$ package. The biosensing device present in the package containing the Ar:$O_2$ mixture turns color faster due to the presence of oxygen. Preparation of a standard curve permits detection of each type of gas mix relative to the other, and also permits detection of a change in oxygen level caused by vegetable respiration.

As another example in the case of a leak, the biosensing device turns color more slowly when placed in a 15 package under 100% krypton than when placed in a package under 100% $N_2$.

EXAMPLE 4

The above mentioned hydrolase system ($\beta$-D-Glucosidase/p-Nitrophenyl-$\beta$-D-Glucopyranoside) is placed inside a 3 cc bag by heat-sealing of the polymeric film used in protocol described above (PE 2 mil).

The protocol followed is the same as described in the third detailed example of the invention, except for the fact that the colorigenic reaction observed is yellow, and is an acceleration rather than an inhibition. Thus, Kr packaged vegetables will produce a yellow color change in the device faster than will nitrogen packaged produce.

Example Results

A selected example is given below for one of the enzymatic system/polymeric film tandems assayed. Given as well is the maximum change in enzymatic activity noted compared to the reaction resulting from air diffusion through the film, or compared to nitrogen. A sample graphic data output file is appended.

Polymeric film insert in diffusion cells: Curlon Grade 861 (CURWOOD).

Biochemical reaction (monitored at 305 nm): Tyrosinase/L-Tyrosine at 25° C. and optimal reaction conditions, gas in upper chamber of the diffusion cell being:

| Reference Air: | |
| --- | --- |
| Ar | −25% |
| Kr | −35% |
| Xe | −30% |
| Reference Nitrogen: | |
| Ar | −21% |
| Kr | −32% |
| Xe | −26% |

Having described the present invention, it will now be apparent to one of ordinary skill in the art that many changes and modifications may be made to the above-described embodiments without departing from the spirit and the scope of the present invention.

What is claimed as new and desired to be secured by letters patent of the united states is:

1. A method of detecting at least one noble gas with an enzyme-based sensor having at least one enzyme therein and having a membrane therefor which is at least semi-permeable to said at least one noble gas, which comprises:
   a) permeating said at least one noble gas through said membrane;
   b) contacting at least one enzyme in said sensor with an amount of said at least one noble gas sufficient to change an activity of said at least one enzyme; and
   c) detecting the change in the activity of said at least one enzyme; and
   wherein said at least one noble gas is selected from the group consisting of xenon, krypton, argon and neon.

2. The method of claim 1, wherein said at least one noble gas is in admixture with a carrier gas selected from the group consisting of $N_2O$, He, $CO_2$, $N_2$, $O_2$ and air in said mixture of gases.

3. The method of claim 1, wherein said at least one noble gas is at a pressure of from about $10^{-2}$ atmospheres to about 10 atmospheres.

4. The method according to claim 1, wherein said at least one noble gas is in gaseous form or liquid form or both and is injected into contact with said at least one enzyme in said sensor.

5. The method according to claim 1, wherein said at least one enzyme in said sensor is saturated to more than 50 volume % of its full saturation level.

6. The method according to claim 5, wherein said at least one enzyme in said sensor is saturated to more than 70% by volume of its full saturation level.

7. The method according to claim 6, wherein said at least one enzyme in said sensor is saturated to more than 80% by volume of its full saturation level.

8. The method according to claim 2, wherein said admixture contains, in addition to said at least one noble gas, less than 50% by volume of oxygen, carbon dioxide or a mixture thereof.

9. The method according to claim 8, wherein said admixture contains, in addition to said at least one noble gas, less than 30% by volume of oxygen, carbon dioxide or a mixture thereof.

10. The method according to claim 9, wherein said admixture contains, in addition to said at least one noble gas, less than 20% by volume of oxygen, carbon dioxide or a mixture thereof.

11. The method according to claim 10, wherein said admixture contains, in addition to said at least one noble gas, less than 10% by volume of oxygen, carbon dioxide or a mixture thereof.

12. The method according to claim 1, wherein said at least one noble gas is about 90% to 99% by volume of argon and 1% to 10% by volume of Xe or Kr or both.

13. The method according to claim 2, wherein said admixture contains about 50% by volume of Ne and 50% by volume of He.

14. The method according to claim 2, wherein said at least one noble gas comprises about 5% to 10% by volume of Xe and 90% to 95% by volume of Kr.

15. The method according to claim 2, wherein said admixture contains less than 2% by volume of argon, oxygen, nitrogen or a mixture thereof.

16. The method according to claim 1, wherein the temperature at which said at least one enzyme in said sensor is contacted with said at least one noble gas is between 0° C. and 40° C.

17. The method according to claim 1, wherein the temperature at which said at least one enzyme in said sensor is contacted with said at least one noble gas is between 10° C. and 30° C.

18. The method according to claim 1, wherein the pressure of the at least one noble gas is less than 10 atmospheres.

19. The method according to claim 18, wherein the pressure of the at least one noble gas is less than 3 atmospheres.

20. The method according to claim 19, wherein the pressure of the at least one noble gas is between 1 and 2 atmospheres.

21. The method according to claim 20, wherein the pressure of said at least one noble gas is about 1 atmosphere.

22. The method of claim 1, which comprises passing said at least one noble gas into a reaction space or medium from through said semi-permeable membrane, said reaction space or medium containing said at least one enzyme; allowing said at least one noble gas effect substantial saturation of the reaction space or medium; and maintaining said substantial saturation for a time sufficient for said at least one enzyme to detect said at least one noble gas.

* * * * *